United States Patent
White et al.

(10) Patent No.: US 9,103,261 B1
(45) Date of Patent: *Aug. 11, 2015

(54) DEVICE AND METHOD FOR ADJUSTING DOSAGE OF FUEL ADDITIVE BASED ON IN-SITU MEASUREMENT OF ADDITIVE AND CONTAINMENT CONCENTRATION

(75) Inventors: James R. White, San Mateo, CA (US); Colin T. Elliott, San Francisco, CA (US)

(73) Assignee: Active Spectrum, Inc., Foster City ( * ) Notice: Subject to any disclaimer, the term of this patent is extended or adjusted under 35 U.S.C. 154(b) by 732 days.

This patent is subject to a terminal disclaimer.

(21) Appl. No.: 13/094,552

(22) Filed: Apr. 26, 2011

Related U.S. Application Data

(63) Continuation of application No. 12/906,822, filed on Oct. 18, 2010, now Pat. No. 8,648,596, which is a continuation-in-part of application No. 11/983,393, filed on Nov. 8, 2007, now Pat. No. 7,868,616, which is a continuation-in-part of application No. 11/590,522, filed on Oct. 31, 2006, now Pat. No. 7,589,529.

(60) Provisional application No. 60/736,264, filed on Nov. 14, 2005, provisional application No. 61/328,331, filed on Apr. 27, 2010.

(51) Int. Cl.
*F02B 43/00* (2006.01)
*F01N 11/00* (2006.01)

(52) U.S. Cl.
CPC ..................... *F01N 11/00* (2013.01)

(58) Field of Classification Search
USPC .......... 123/1 A; 324/316, 200, 214, 306, 318, 324/300
See application file for complete search history.

(56) References Cited

U.S. PATENT DOCUMENTS

| | | | |
|---|---|---|---|
| 3,817,722 A | 6/1974 | Scott et al. | |
| 3,926,577 A | 12/1975 | Zetlmeisl et al. | |
| 4,659,339 A * | 4/1987 | May et al. | 44/320 |
| 5,169,785 A * | 12/1992 | Altman et al. | 436/60 |
| 8,212,563 B2 * | 7/2012 | White et al. | 324/316 |
| 2007/0240649 A1* | 10/2007 | Freeman | 123/1 A |
| 2008/0164874 A1* | 7/2008 | White et al. | 324/316 |

OTHER PUBLICATIONS

Premovic, P.I. et al, "Estimation of vanadyl porphyrin concentration in sedimentary kerogens and asphaltenes," Fuel 79 (2000) 813-819.
Premovic, P.I. and Hocking, M.B., "Coal inclusions of the Athabasca tar sands: characterization and direct determination of vanadyl porphyrin content by electron spin resonance," Geochimica et Cosmochimica Acta. 1978, vol. 42, pp. 359-365.
Moore, J.W. and Dunning, H.N. "Metal porphyrin complexes in an asphaltic midcontinent crude oil." US Bureau of Mines Report of Investigations 5370, Washington DC, 1957.
(Continued)

*Primary Examiner* — Lindsay M. Low
*Assistant Examiner* — Ruben Picon-Feliciano
(74) *Attorney, Agent, or Firm* — Tope-McKay & Associates

(57) ABSTRACT

A device and method for adjusting dosage of a fuel additive is described. The device includes a fuel reservoir and an additive reservoir. A variable-flow pump is used to pump the additive into contact with the fuel to create a combined fluid. An ESR sensor is positioned downstream from the pump and fuel reservoir such that a portion of the combined fluid passes through the ESR sensor, which measures the concentration of contaminants and fuel additive in the fuel. Based on the concentrations, a controller controls the rate at which the fuel additive is pumped, thereby adjusting the dosage of the fuel additive.

8 Claims, 5 Drawing Sheets

(56) References Cited

OTHER PUBLICATIONS

Yen T.F. et al, "Investigation of the nature of free radicals in petroleum asphaltenes and related substances by electron spin resonance," Anal. Chem. 34, 1962, pp. 694-700.

"Measure Vandium, Asphaltene Concentration from the Field." E&P, Apr. 2009, pp. 103-104.

"ESR Tackles Process Stream Analysis" Technology, C&EN, Oct. 1, 1962, pp. 48-50.

* cited by examiner

DEVICE AND METHOD FOR ADJUSTING DOSAGE OF FUEL ADDITIVE BASED ON IN-SITU MEASUREMENT OF ADDITIVE AND CONTAINMENT CONCENTRATION

CROSS-REFERENCE TO RELATED APPLICATIONS

This is a Continuation-in-Part application of U.S. Non-Provisional application Ser. No. 12/906,822, filed on Oct. 18, 2010, which is Continuation-in-Part application of U.S. Non-Provisional application Ser. No. 11/983,393, filed on Nov. 8, 2007, now patented as U.S. Pat. No. 7,868,616, which was a Continuation-in-Part application of U.S. Non-Provisional application Ser. No. 11/590,522, filed on Oct. 31, 2006, now patented as U.S. Pat. No. 7,589,529, which was Non-Provisional Application of U.S. Provisional Application No. 60/736,264, filed on Nov. 14, 2005. This is ALSO a Non-Provisional Utility Patent Application of U.S. Provisional Application No. 61/328,331, filed on Apr. 27, 2010, entitled, "Method of Adjusting Dosage of Fuel Additive Based on In-Situ Measurement of Additive and Contaminant Concentration."

BACKGROUND OF THE INVENTION (1) Field of Invention

The present invention relates to a fuel additives and, more specifically, to a device and method for adjusting the concentration of fuel additive in a hydrocarbon fuel based on simultaneous measurement of the concentration of impurities and additives in the fuel.

(2) Description of Related Art

In the field of fuel additives, it is desirable to inhibit corrosion resulting from the presence of vanadium in hydrocarbon fuels, such as those fuels used in gas turbines and diesel engines. As is widely known, vanadium compounds, in particular vanadyl porphyrins, are naturally occurring in crude oil, heavy fuel oil and related residual fuels (hereafter referred to as "fuel oil") used to power gas turbines, boilers, diesel engines and similar industrial power-generation equipment (hereafter referred to as "the equipment"). When burned, the Vanadium contaminant forms various vanadium oxides which can cause accelerated corrosion of the metal surfaces in the equipment, such as turbine blades in gas turbines and exhaust valves in diesel engines.

It is widely known that the addition of magnesium-based fuel additives can inhibit the formation of damaging vanadium compounds during combustion and substantially extend the life of the gas turbine or diesel engine, as cited in literature reference numbers 1, 2, and 3 (See the "List of Cited References" below). An example of a commercially available magnesium-based fuel additive is "LMG-30E," as provided by Liquid Minerals Group, Inc., which located at P.O. Box, 1700, New Waverly, Tex., 77538.

These additives have various proprietary compositions in addition to magnesium, including silicon, aluminum, chromium and other transition-metal compounds, sulphonates and oxides thereof. Typically, in the case of a gas turbine, the equipment operator will test the fuel for contaminants, including vanadium, sodium, potassium and other elements at a specified interval (e.g., every 8 hours) and adjust the rate at which magnesium additive is introduced into the inlet fuel flow based on the concentration of vanadium measured. Magnesium is typically added in the ratio of 3:1 (magnesium: vanadium) by metal weight, although other ratios can be used in some circumstances, for example 3.5:1. However, it is understood that too little magnesium fuel additive will adversely increase the rate of corrosion of the turbine blades, while too much magnesium additive will add cost and result in increased ash buildup, thereby reducing efficiency unnecessarily. It is therefore desirable to precisely monitor the level of vanadium and magnesium additive in the fuel to obtain an optimal operating condition at all times.

The typical method of operation, in which contaminant levels are measured every few hours, can result in substantial errors in fuel additive dosage. This method of operation can be characterized as "open-loop" in the sense that changes in fuel composition or additive dosage rate cannot be detected except when a sample is drawn from the fuel flow and tested in an on-site laboratory. One typical test method is spark emission tomography. This open-loop mode of operation cannot ensure that the equipment is properly protected from excessive contaminant levels at all times.

Thus, a continuing need exists for a device and method that solves the problems of the prior art by continuously and simultaneously monitoring the level of vanadium contaminant and magnesium additive in the inlet fuel stream.

SUMMARY OF INVENTION

The present invention relates to device and method for adjusting dosage of a fuel additive based on in-situ measurements of additive and contaminant concentration. The device includes a first reservoir (e.g., fuel reservoir) holding a first fluid (e.g., hydrocarbon fuel) for dispensing therefrom. A second reservoir (e.g., additive reservoir) is included for holding a second fluid (e.g., fuel additive) for dispensing therefrom. A flow control (e.g., variable-flow pump) is fluidically connected with the second reservoir to control a rate of second fluid dispensed from the second reservoir. It should be noted that the term "fluidically connected" as used herein refers to components that are connected (either directly or indirectly) in such a manner that a fluid can pass therebetween, through the use of piping, hosing, valves, flow controls, etc.

Additionally, the first reservoir is fluidically connected with the flow control such that the second fluid dispensed from the second reservoir and passing through the flow control combines with the first fluid dispensed from the first reservoir to form a combined fluid. An electron spin resonance (ESR) sensor is positioned downstream from the flow control and first reservoir such that a portion of the combined fluid passes through the ESR sensor. The ESR sensor operable for measuring material within the combined fluid, such as concentrations of contaminants and fuel additives within a hydrocarbon fuel.

A controller is communicatively connected with the ESR sensor and the flow control. The controller is operable for receiving a signal regarding the material within the combined fluid and controlling, via the flow control, a rate at which the second fluid is dispensed from the second reservoir. It should be noted that the term "communicatively connected" as used herein generally refers to components that are connected with one another in such a manner that they can communicate with one another, either directly or indirectly; examples of such a communicative connection is through wired or wireless connections.

A restrictor can be included such that it is fluidically connected with the ESR, the fuel reservoir, and the variable-flow pump to cause a portion of the combined fuel to pass through the ESR.

The ESR is of a size that it allows for in-situ, real-time operations. For example, the ESR has dimensions of less than 3 feet wide, by 3 feet tall, by 3 feet deep, and desirably 12 inches by 8 inches by 4 inches.

Finally, as can be appreciated by one in the art, the present invention also comprises a method for forming and using the invention described herein. For example, the method for adjusting dosage of a fuel additive comprises acts of simultaneously measuring, in-situ, a concentration of a contaminant and a fuel additive in a hydrocarbon fuel; and adjusting a rate at which fuel additive is introduced into the hydrocarbon fuel in real-time, based on the measurement of contaminant concentration and fuel additive concentration, thereby maintaining an optimal ratio of contaminant to fuel additive at all times.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
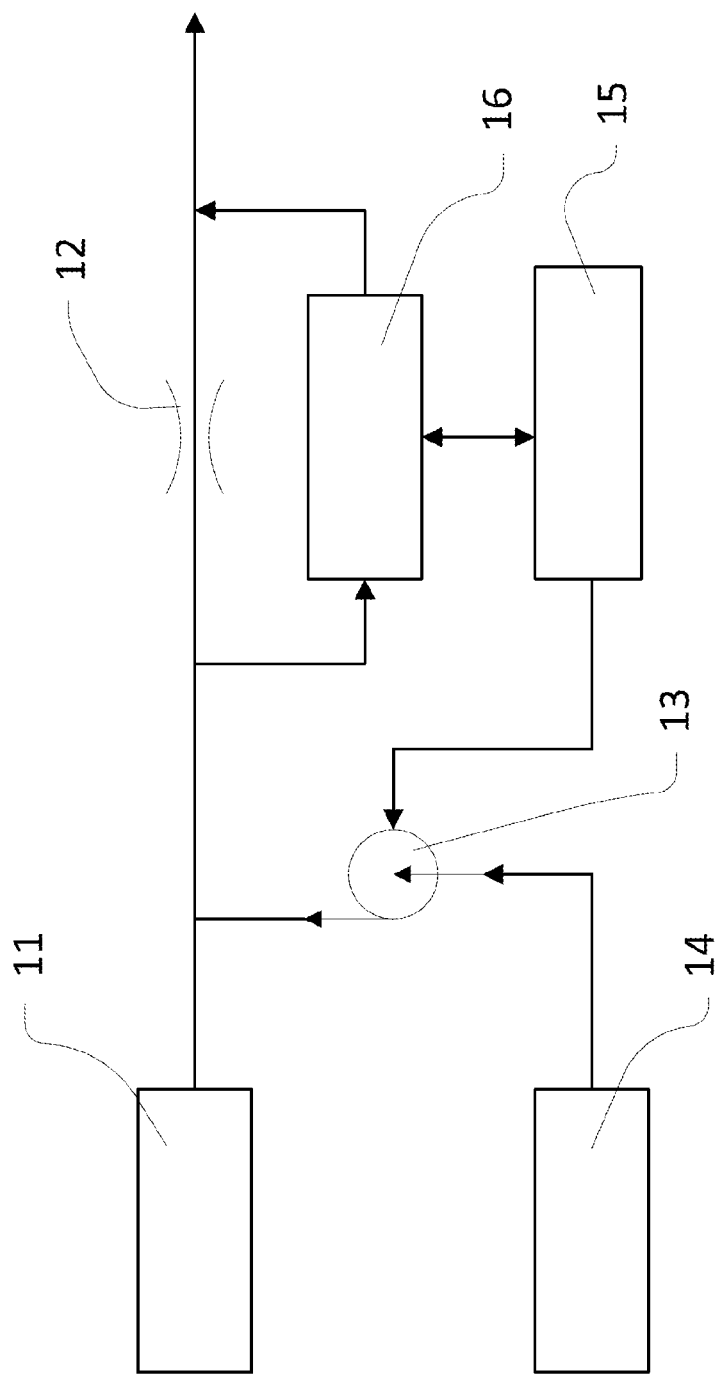
FIG. 1 is an illustration depicting a closed-loop fuel additive control system according to the present invention.

The present invention relates to a device and method for adjusting the concentration of fuel additive in a hydrocarbon fuel based on simultaneous measurement of the concentration of impurities and additives in the fuel. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

Before describing the invention in detail, first a list of cited references is provided. Subsequently, an introduction provides the reader with a general understanding of the present invention. Next, specific details of the present invention are provided to give an understanding of the specific aspects. Finally, a summary is provided as a synopsis of the present invention.

(1) List of Cited Literature References

The following references are cited throughout this application. For clarity and convenience, the references are listed herein as a central resource for the reader. The following references are hereby incorporated by reference as though fully included herein. The references are cited in the application by referring to the corresponding literature reference number.

1. U.S. Pat. No. 3,817,722, issued to Scott. J. F. et. al;
2. U.S. Pat. No. 4,659,339, issued to May, W. R. and Zetlmeisl, M. J.;
3. U.S. Pat. No. 3,926,577, issued to Zetlmeisl et. al;
4. Premovic, P. I. et al, "Estimation of vanadyl porphyrin concentration in sedimentary kerogens and asphaltenes," Fuel 79 (2000) 813-819;
5. Premovic, P. I. and Hocking, M. B., "Coal inclusions of the Athabasca tar sands: characterization and direct determination of vanadyl porphyrin content by electron spin resonance," Geochimica et Cosmochimica Acta. 1978, vol. 42, pp. 359-365;
6. Moore, J. W. and Dunning, H. N. "Metal porphyrin complexes in an asphaltic midcontinent crude oil." US Bureau of Mines Report of Investigations 5370, Washington D.C., 1957; and
7. Yen T. F. et al, "Investigation of the nature of free radicals in petroleum asphaltenes and related substances by electron spin resonance," Anal. Chem. 34, 1962, pp. 694-700.

(2) Introduction

The present invention relates to the inhibition of corrosion resulting from the presence of vanadium in hydrocarbon fuels, such as those fuels used in gas turbines and diesel engines. As is widely known, vanadium compounds, in particular vanadyl porphyrins, are naturally occurring in crude oil, heavy fuel oil and related residual fuels (hereafter referred to as "fuel oil") used to power gas turbines, boilers, diesel engines and similar industrial power-generation equipment (hereafter referred to as "the equipment"). When burned, the Vanadium contaminant forms various vanadium oxides which can cause accelerated corrosion of the metal surfaces in the equipment, in particular turbine blades in gas turbines, and exhaust valves in diesel engines. This type of corrosion is sometimes referred to as "hot corrosion." To inhibit such corrosion, the present invention is directed to a device and method for simultaneously measuring the concentration of vanadium contaminant and magnesium additive, and adjusting the concentration of magnesium fuel additive based on simultaneous measurement of both quantities.

This method of measuring, in-situ, both the concentration of vanadium and the concentration of magnesium additive in real-time offers several advantages over the prior art, such as:
1. The test is nondestructive and consumes no reagents.
2. The electron spin resonance (ESR) equipment employed can operate unattended.
3. The test is relatively rapid (on the order of one to ten minutes) and can run continuously.
4. "Closed-loop" control is possible, in which the rate at which additive is introduced into the fuel oil is continuously varied in response to changes in the vanadium concentration measured in the fuel oil.
5. The ratio of additive to vanadium in the fuel can be measured in real-time and kept at a constant level using feedback control of the fuel additive pump.

The simultaneous, in-situ measurement technique disclosed herein can therefore optimize the amount of fuel additive consumed in equipment in real-time, minimizing additive costs while optimally protecting the equipment from damage.

(3) Specific Details

The present invention provides for the simultaneous, in-situ measurement of both the concentration of vanadium and the concentration of magnesium additive in real-time. For example and as depicted in FIG. 1, the present invention includes a device that is used in order to perform the simultaneous, in-situ measurement. In this example, fuel flows from the fuel reservoir 11 (e.g., first reservoir), and is combined with an additive, pumped from the additive reservoir 14 (e.g., second reservoir) using a flow control 13 (e.g., variable-flow pump). It should be understood that although the flow control 13 is described as a variable-flow pump, the present invention is not intended to be limited thereto as it is any suitable mechanism or device that allows for the selective control of the amount of fluid that flows or is pumped from the additive reservoir, non-limiting examples of which include valves, pumps, etc.

The flow of fuel plus the additive (i.e., combine fluid) is partially diverted through the electron spin resonance (ESR) sensor 16, where the concentration of materials (e.g., contaminant and additive) is measured simultaneously as described below. The resulting concentration measurements are interpreted by the controller 15, which in turn controls the rate at which additive is pumped into the fuel flow. The controller 15 is any suitable controller that allows for control of the rate at which the additive is pumped into the fuel flow, a non-limiting example of which includes the PXI Embedded Controller as sold by the National Instruments Corporation, located at 11500 North Mopac Expressway, Austin, Tex. 78759-3504.

A restrictor 12 ensures that some fraction of the flow is forced through the ESR sensor 16. The ESR sensor 16 is any suitable ESR spectrometer (e.g., miniature ESR) that provides for in-situ, real-time measurement. In other words, it must be suitably sized to allow for convenient installation in a variety of applications. A non-limiting example of a suitable size is an ESR with dimensions of less than 3 feet wide by 3 feet tall by 3 feet deep. For example, the ESR sensor can have dimensions of approximately 12 inches by 8 inches by 4 inches, such as the Micro-ESR sold by Active Spectrum Inc., located at 1191 Chess Drive, Suite F, Foster City, Calif. 94404. Because the ESR sensor 16 is downstream from the fuel reservoir 11 and additive reservoir 14, the ESR sensor 16 can measure in-situ, the concentration of contaminant and additive in real-time and adjust the additive as desired. It should be noted that as an alternative to ESR spectrometry, magnetic resonance spectroscopy can also be employed within the scope of the present invention to adjust the dosage of the additive as desired.

Described below is the method by which the device of the present invention can be employed to measure and adjust the dosage of the fuel additive.

It is widely recognized in the scientific literature that vanadyl porphyrins in crude oil have a characteristic electron spin resonance (ESR/EPR) spectrum that uniquely identifies the presence of vanadyl in crude oil (see literature reference nos. 4, 5, 6, and 7). Such a spectrum can be created by taking measurements with the ESR sensor 16. An example is shown in FIG. 2, in which the ESR spectra of six crude oils have three distinct peaks in the range g=1.9 to g=2.2.

Figure 2:
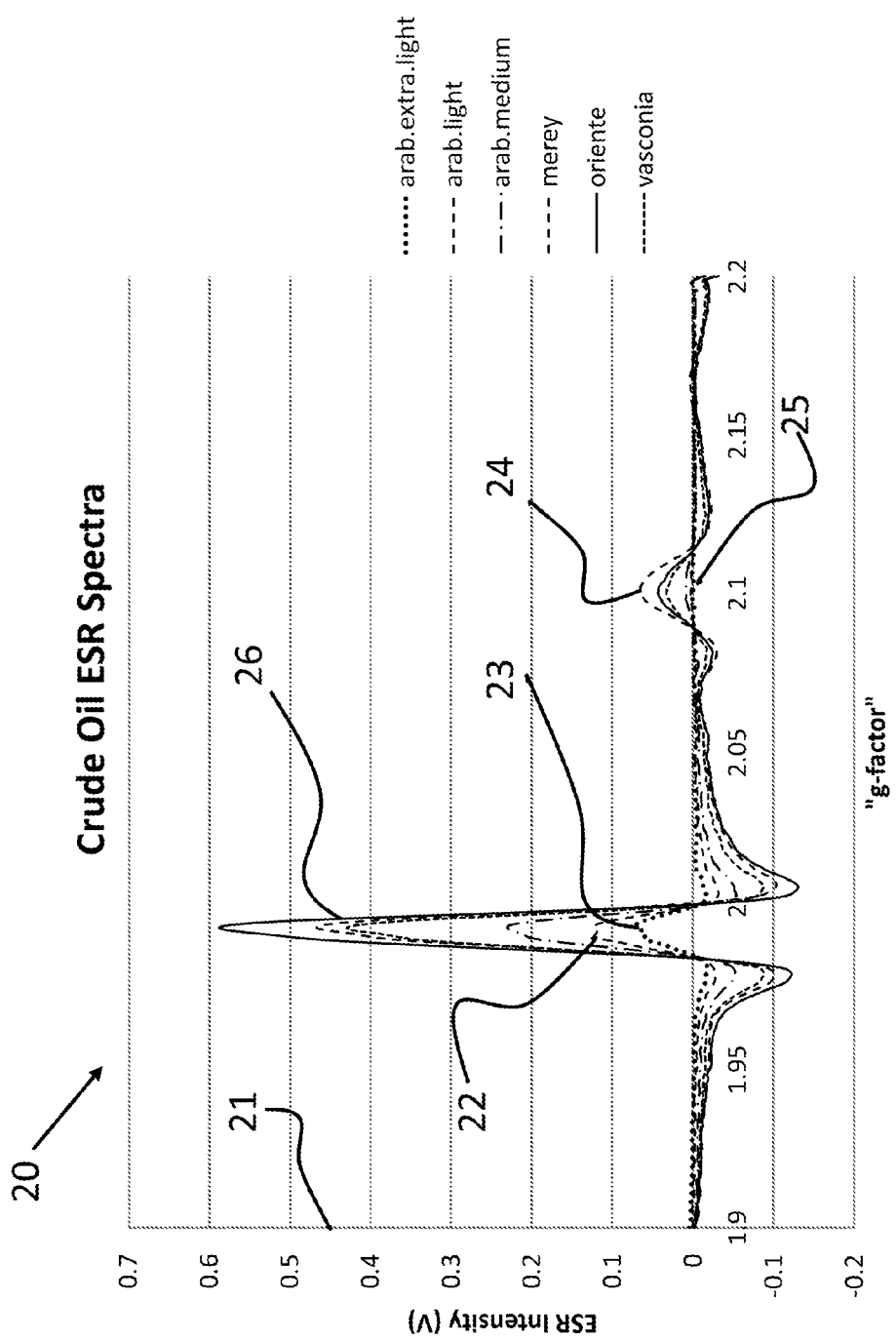
FIG. 2 is a graph depicting a typical electron spin resonance (ESR) spectra of crude oil.
Figure 3:
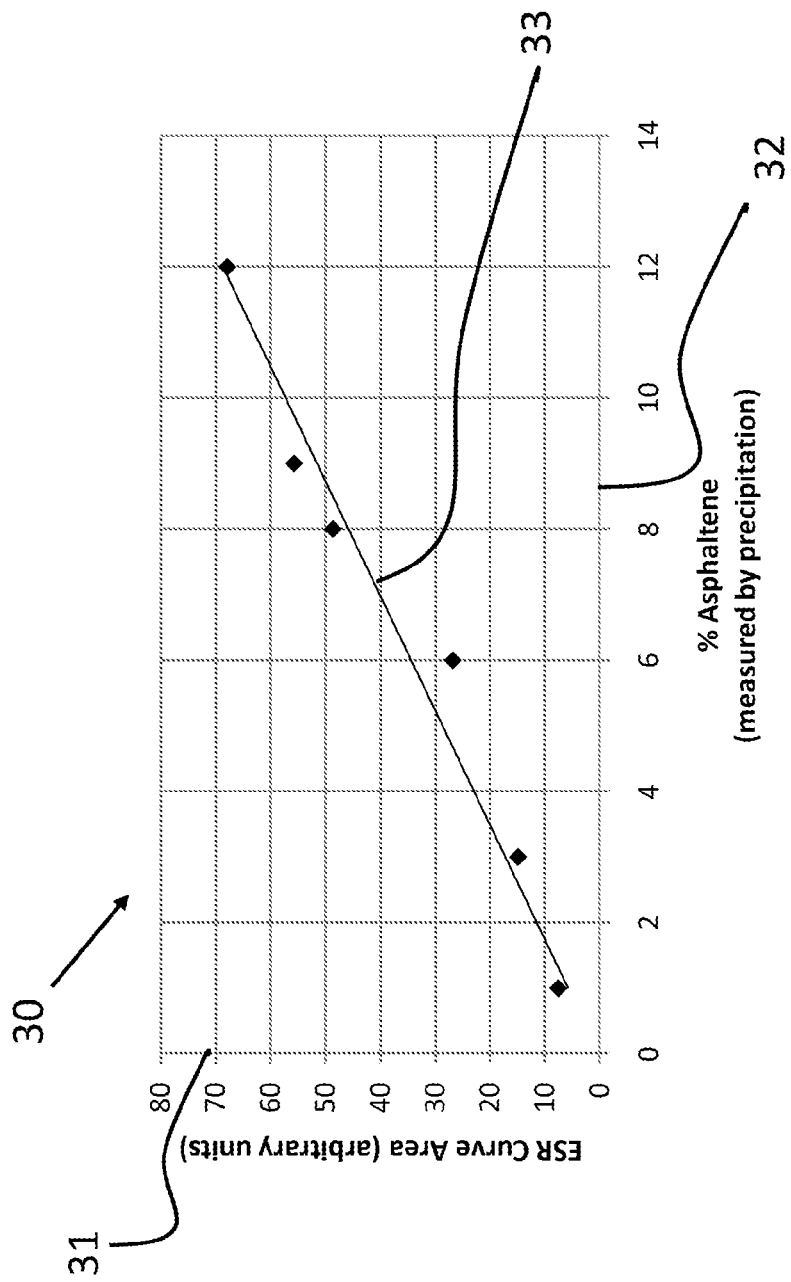
FIG. 3 is a graph illustrating a relationship between area under the central ESR peak and asphaltene concentration measured by precipitation.
Figure 4:
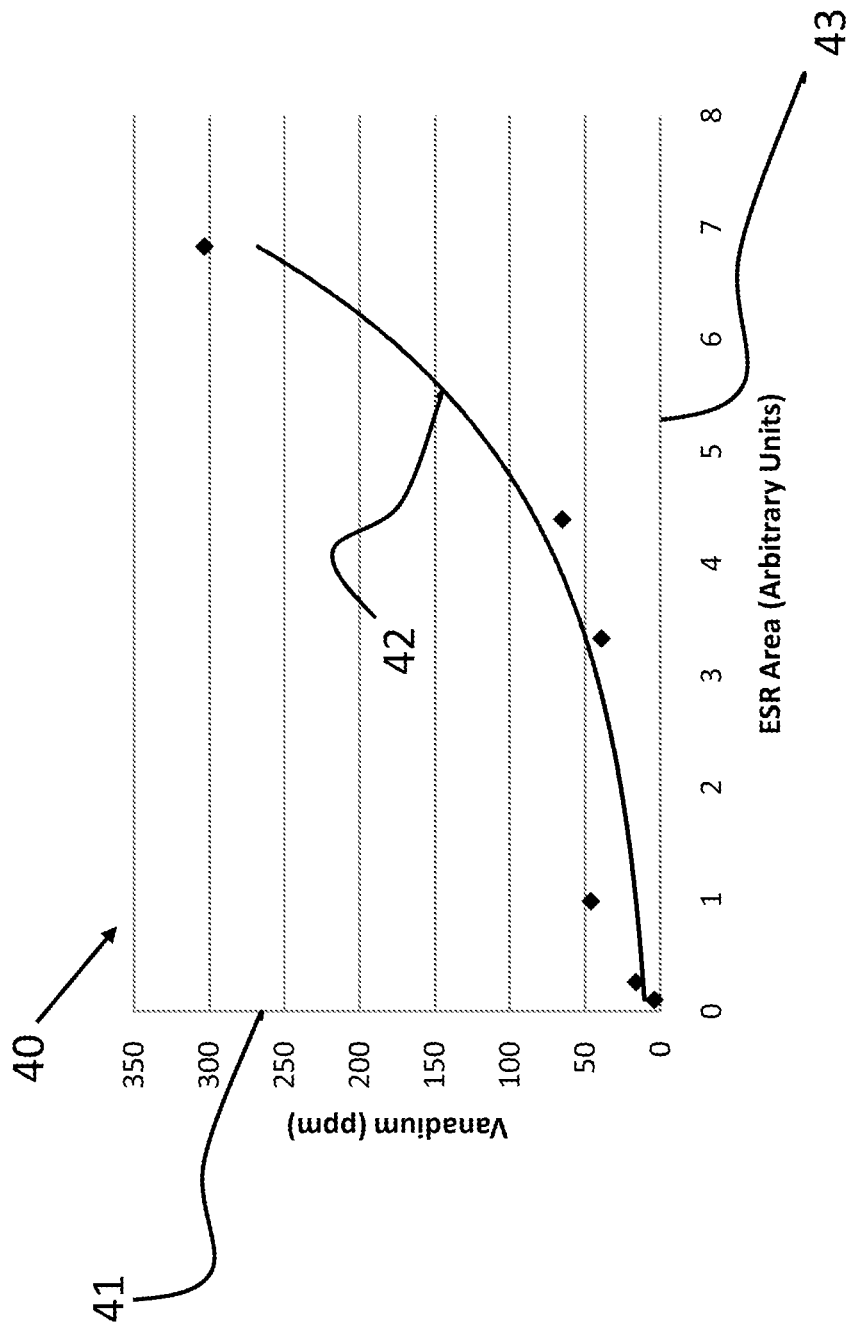
FIG. 4 is a graph illustrating a relationship between area under the g=2.10 ESR peak and vanadium concentration measured by inductively coupled plasma (ICP)

FIG. 2 shows a chart 20, having a vertical axis 21 depicting the intensity of the electron spin resonance signal in arbitrary units and a horizontal axis 25 showing g-factor, or equivalently, a magnetic field. The large central peak is a superposition of a leftmost peak 22 and a rightmost peak 23. The leftmost peak 22 is due to vanadyl (vanadium) and the rightmost peak 23 is due to asphaltene. A second peak 24 is identified as being due to hyperfine splitting of the vanadyl ion present in the crude oil. In order to analyze the concentration of vanadium and asphaltene in the oil, the area under each peak must be computed. For example, the area under the central peaks 22 and 23 can be computed and correlated to the concentration of asphaltene, as shown in FIG. 3. The area under the rightmost peak 24 can be computed and correlated to the amount of vanadium in the sample, as shown in FIG. 4.

The signal as depicted in FIG. 2 can be used to measure vanadium concentration of crude oil, heavy fuel oil and related fuels. Typical signal analysis techniques include measurement of the area under each peak attributable to either vanadyl or asphaltene (the organic radical at g=2.0032 is normally attributed to asphaltenes in the oil). Another approach is curve-fitting, where each free radical is assumed to contribute a derivative of a Lorentzian lineshape to the resulting spectrum, as in Equations 1 and 2.

$$X'(\omega) = \frac{\left(\frac{1}{2}\right)|\gamma|(\omega_0 - \omega)T_2^2 M_0}{1 + (\omega - \omega_0)^2 T_2^2 + \left(\frac{1}{4}\right)\gamma^2 H_1^2 T_1 T_2} \quad (1)$$

$$X''(\omega) = \frac{\left(\frac{1}{2}\right)|\gamma|T_2 M_0}{1 + (\omega - \omega_0)^2 T_2^2 + \left(\frac{1}{4}\right)\gamma^2 H_1^2 T_1 T_2} \quad (2)$$

These equations are generally known as the Bloch equations for a two-state system. Here, $\gamma$ is the magnetogyric ratio, $M_0$ is the magnetization, $T_1$ is the "spin-lattice" relaxation time, $T_2$ is the "spin-spin" relaxation time, $H_1$ is the amplitude of the RF magnetic field and $\omega$ is frequency.

After the center field, line width and amplitude of each resonance have been determined, the area under to each resonance can be computed. The area under each resonance is a function of the concentration of free radicals in the oil. An example of this computation is shown in FIG. 3 and FIG. 4, for vanadium and asphaltene free radicals.

The asphaltene and vanadium concentrations of the crude oils tested in this case are tabulated in Table 1 below.

TABLE 1

Properties of selected crude oils.

|  | Asphaltene % | Vanadium (ppm) |
|---|---|---|
| Arab Extra Light | 1 | 3.7 |
| Arab Light | 3 | 16 |
| Arab Medium | 6 | 46 |
| Vasconia | 8 | 39 |
| Merey | 9 | 303 |
| Oriente | 12 | 65 |

FIG. 3 shows a chart 30 with a vertical axis 31 showing ESR intensity in arbitrary units and a horizontal axis 32 showing asphaltene percentage as derived from assay data in Table 1. A line 33 depicts a relationship between the ESR intensity and asphaltene percentage, although it is understood that many such lines could be constructed depending on the sensitivity and calibration of the ESR instrument in question. Based on the data in FIG. 3, the sensitivity limit of the ESR technique is approximately 0.5% asphaltene, although future improvements in the construction of the device could lead to substantially better performance in terms of sensitivity.

FIG. 4 depicts a chart 40 with a vertical axis 41 depicting vanadium concentration in parts-per-million (ppm) and a horizontal axis 43 depicting ESR intensity in arbitrary units. In this case, the data on line 43 refers to the area under the rightmost peak 14 at ~g=2.10 in FIG. 2 and therefore refers to the concentration of vanadium only. A line 42 is fitted to the measured data, providing a relationship between vanadium concentration and ESR intensity, although it is understood that many such lines could be constructed depending on the sensitivity and calibration of the ESR instrument in question. The sensitivity limit of the ESR device in this example is approximately 1 ppm Vanadium, although it is understood that other instruments can yield substantially higher sensitivity, some having been documented with a sensitivity limit as low as 0.1 ppm.

The inventor of the present invention has discovered that the magnesium additives commonly used to treat heavy fuel oil also have a characteristic ESR spectrum, attributable to the presence of naturally occurring $^{25}$Mg impurities, manganese ($Mn^{2+}$) and, in some cases, $Cr^{3+}$, $Fe^{2+}$, $Fe^{3+}$ and other transition-metal species incorporated into the fuel additive. A typical ESR spectrum of a fuel additive, LMG-30E, is shown in FIG. 5.

Figure 5:
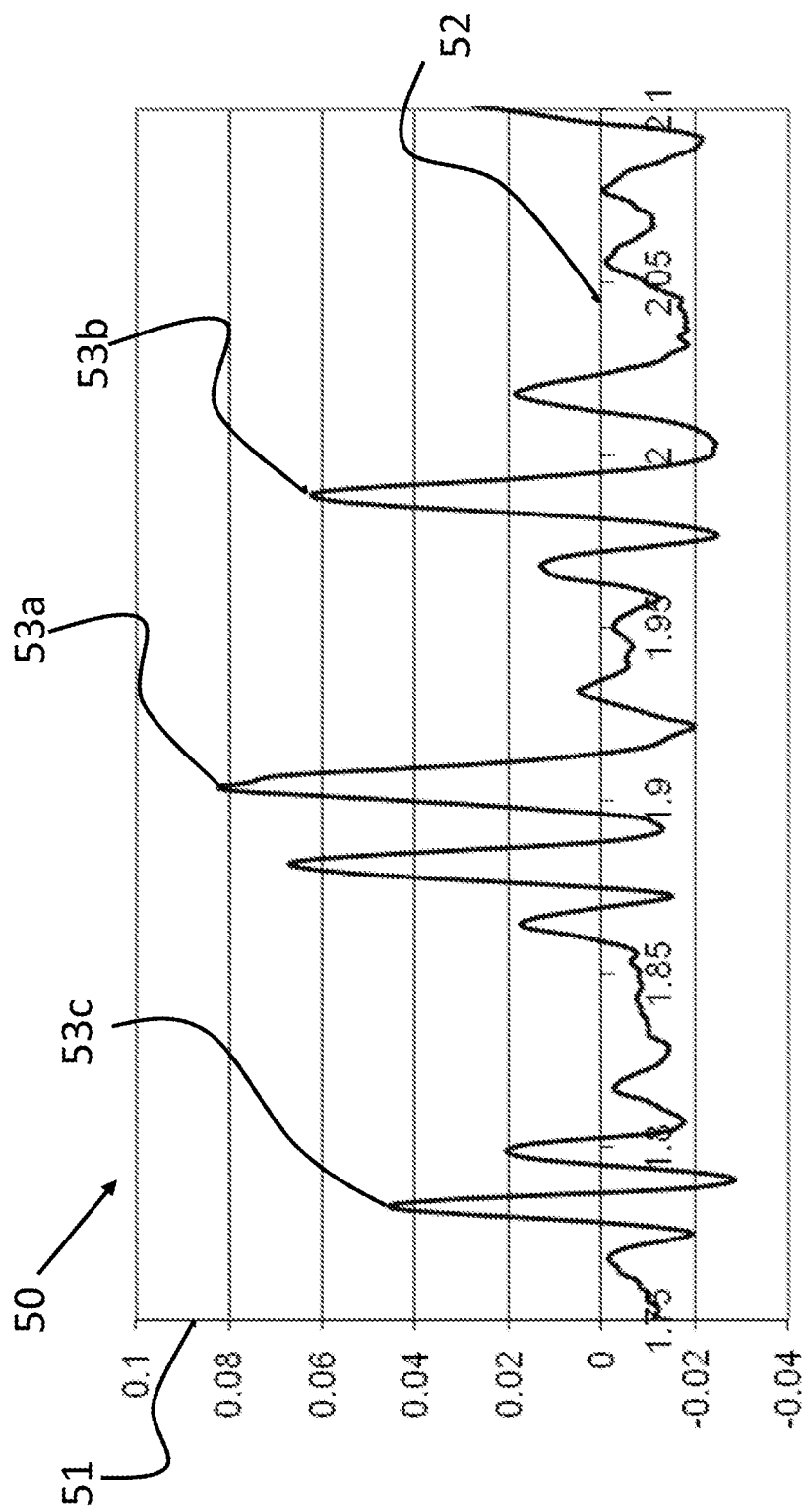
FIG. 5 is a graph illustrating an ESR spectrum of a magnesium-based fuel additive.

In FIG. 5, a chart 50 having vertical axis 51 depicting ESR intensity in arbitrary units and horizontal axis 52 depicting g-factor, shows a characteristic ESR spectrum of fuel additive mixed into a distillate oil with no ESR spectrum. A plurality of peaks, among them 53a, 53b and 53c are visible which uniquely identify the presence of a fuel additive in the oil. In the case of this instrument, the signal-to-noise is approximately 100, for a 30% fuel additive concentration, although it is understood that other instruments with superior signal-to-noise characteristics may be employed to make this measurement with significantly improved sensitivity. The ultimate sensitivity limit of the ESR technique for measuring fuel additive concentration is better than 3 ppm.

The fuel additive is prepared by suspending solid particles of additives in a light oil base that is readily miscible with fuel oil. This spectrum has 14 ESR peaks in the range of g=75 to g=2.15. A more complete ESR spectrum (which covers a wider range of magnetic fields) might be advantageous in determining the composition of the additive more precisely, however, the ESR spectrum shown in FIG. 5 is adequate to uniquely identify the presence of the additive in a typical fuel oil sample. Furthermore, it is noted that different fuel additives may have differing ESR spectra depending on their exact chemical composition.

Similar signal-analysis techniques to those used for analysis of untreated crude oil may be applied to mixtures of crude oil and additive, thus allowing the determination of the ratio of vanadium to magnesium additive in-real time. In this case, the area under each of the 14 peaks attributed to fuel additive must be computed, and then compared to the area under the three vanadium and asphaltene peaks that are naturally occurring in the fuel oil.

It is understood that the above-described preferred embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claim rather than by the foregoing description. All changes which come within the meaning and range of equivalency of the claims are to be embraced within their scope.

(4) Summary

The present invention is directed to a device and method for simultaneously measuring the concentration of contaminants and fuel additives in a hydrocarbon fuel feedstock for use in a gas turbine or diesel engine. Specifically, an in-situ electron spin resonance spectrometer can be used operating at 3.4 GHz to measure both vanadium, asphaltene and magnesium-based fuel additive concentrations simultaneously. The data can be used to control the rate at which a pump introduces fuel additive into the fuel flow, thereby optimizing the consumption of expensive additive and minimizing costs for the equipment operator. However, other in-situ electron spin resonance spectrometers can be envisioned, having various improvements such as larger sample chambers or higher operating frequencies that will yield yet further improvements in the sensitivity of this technique. Further, it should be noted that the device according to the present invention can be used to measure other materials and in other applications, while remaining within the scope of this invention.

What is claimed is:

1. A device for adjusting dosage of an additive, comprising:
  a first reservoir holding a first fluid for dispensing therefrom;
  a second reservoir holding a second fluid for dispensing therefrom;
  a flow control fluidically connected with the second reservoir to control a rate of second fluid dispensed from the second reservoir;
  wherein the first reservoir is fluidically connected with the flow control such that the second fluid dispensed from the second reservoir and passing through the flow control combines with the first fluid dispensed from the first reservoir to form a combined fluid;
  an electron spin resonance (ESR) sensor fluidically connected with at least one of the first and second reservoirs;
  a controller communicatively connected with the ESR sensor and the flow control, the controller operable for receiving a signal from the ESR sensor and controlling, via the flow control, a rate at which the second fluid is dispensed from the second reservoir;

wherein the ESR sensor is positioned downstream from the first reservoir and second reservoir and flow control such that a portion of the combined fluid passes through the ESR sensor, the ESR sensor operable for measuring material within the combined fluid; and wherein the first reservoir is a hydrocarbon fluid reservoir and the second reservoir is an additive reservoir, such that the ESR sensor is adapted to simultaneously measure both contaminant concentration and additive concentration within the combined fluid, with the controller adjusting the rate at which the second fluid is dispensed from the additive reservoir to adjust the additive concentration based on simultaneous measurement of both the contaminant concentration and additive concentration.

2. The device as set forth in claim 1, wherein the controller is operable for receiving a signal regarding the material within the combined fluid and controlling, via the flow control, a rate at which the second fluid is dispensed from the second reservoir.

3. The device as set forth in claim 2, wherein the flow control is a variable-flow pump.

4. The device as set forth in claim 3, further comprising a restrictor fluidically connected with the ESR sensor, the hydrocarbon fluid reservoir, and the variable-flow pump to cause a portion of the combined fuel to pass through the ESR sensor.

5. The device as set forth in claim 4, wherein the ESR sensor has dimensions of less than three feet wide, by three feet tall, by three feet deep.

6. The device as set forth in claim 1, further comprising a restrictor fluidically connected with the ESR sensor, the first reservoir, and the flow control to cause a portion of the combined fuel to pass through the ESR sensor.

7. The device as set forth in claim 1, wherein the flow control is a variable-flow pump.

8. The device as set forth in claim 1, wherein the ESR sensor has dimensions of less than three feet wide, by three feet tall, by three feet deep.

* * * * *